United States Patent [19]

Schulz

[11] Patent Number: 5,622,170
[45] Date of Patent: Apr. 22, 1997

[54] APPARATUS FOR DETERMINING THE POSITION AND ORIENTATION OF AN INVASIVE PORTION OF A PROBE INSIDE A THREE-DIMENSIONAL BODY

[75] Inventor: Waldean A. Schulz, Boulder, Colo.

[73] Assignee: Image Guided Technologies, Inc., Boulder, Colo.

[21] Appl. No.: 317,805

[22] Filed: Oct. 4, 1994

Related U.S. Application Data

[63] Continuation of Ser. No. 52,042, Apr. 22, 1993, abandoned, which is a continuation-in-part of Ser. No. 909,097, Jul. 2, 1992, Pat. No. 5,383,454, which is a continuation-in-part of Ser. No. 600,753, Oct. 19, 1990, abandoned.

[51] Int. Cl.⁶ .................................................. A61B 17/00
[52] U.S. Cl. .................... 128/653.1; 606/130; 356/141.1; 356/375
[58] Field of Search ......................... 606/130; 128/653.1; 364/413.22; 356/375, 141.1–141.3, 152.1

[56] References Cited

U.S. PATENT DOCUMENTS

| | | |
|---|---|---|
| 4,209,254 | 6/1980 | Reymond et al. . |
| 4,396,945 | 8/1983 | DiMatteo et al. . |
| 4,419,012 | 12/1983 | Stephenson et al. . |
| 4,585,350 | 4/1986 | Pryor . |
| 4,638,798 | 1/1987 | Shelden et al. . |
| 4,651,732 | 3/1987 | Frederick . |
| 4,706,665 | 11/1987 | Gouda . |
| 4,722,056 | 1/1988 | Roberts et al. . |
| 4,723,544 | 2/1988 | Moore et al. . |
| 4,750,487 | 6/1988 | Zanetti . |
| 4,791,934 | 12/1988 | Brunnett . |
| 4,805,615 | 2/1989 | Carol . |
| 4,809,694 | 3/1989 | Ferrara . |
| 4,836,778 | 6/1989 | Baumrind et al. . |
| 4,875,478 | 10/1989 | Chen . |
| 4,931,056 | 6/1990 | Ghajar et al. . |
| 4,941,967 | 7/1990 | Mannetje et al. . |
| 5,059,789 | 10/1991 | Salcudean . |
| 5,198,877 | 3/1993 | Schulz ..................................... 356/375 |
| 5,299,288 | 3/1994 | Glassman et al. ..................... 606/130 |
| 5,305,091 | 4/1994 | Gelbart et al. . |
| 5,309,913 | 5/1994 | Kormos et al. .......................... 606/130 |
| 5,383,454 | 1/1995 | Bucholz . |

FOREIGN PATENT DOCUMENTS

WO92/06645  4/1992  WIPO .

OTHER PUBLICATIONS

"Real–Time, Noninvasive Recording and Three–Dimensional Display of the Functional Movements of an Arbitrary Mandible Point"; F. Mequi et al.; Proceedings vol. 602, Biostereometrics '85; pp. 77–84.

(List continued on next page.)

*Primary Examiner*—Ruth S. Smith
*Attorney, Agent, or Firm*—Nikaido, Marmelstein, Murray & Oram, LLP

[57] ABSTRACT

System for sensing at least two points on an object for determining the position and orientation of the object relative to another object. Two light emitters mounted in spaced relation to each other on an external portion of an invasive probe remaining outside an object into which an invasive tip is inserted are sequentially strobed to emit light. Three light sensors or detectors, the positions of which are known with respect to a predetermined coordinate system, detect the positions of the two light emitters positioned on the probe. A computer connected to the probe and to the light sensors receives data from the sensors and determines the position and orientation of the probe relative to the predetermined coordinate system. The computer then determines the position and orientation of the invasive portion of the probe inside the object by correlating the position of the invasive portion of the probe relative to the predetermined coordinate system with the position of a model of the object defined in relation to the predetermined coordinate system. A display device connected to the computer indicates the location of the invasive portion of the probe in the object by displaying a representation of the location of the invasive portion of the probe with respect to the model of the object.

7 Claims, 9 Drawing Sheets

OTHER PUBLICATIONS

"Three-Dimensional Stereometric Measurement System Using Optical Scanners, Cylindrical Lenses, and Line Sensors"; Yasuo Yamashita et al.; Proceedings of SPIE, vol. 361; Biostereometrics '82, San Diego, CA. Aug. 1982; pp. 67–73.

"Acquisition and Modeling of Human Body Form Data"; Henry Fuchs, et al.; SPIE vol. 166, NATO Symposium on Applications of Human Biostereometrics, Jul. 1978; pp. 94–102.

SACDAC User's Guide; Version 2e, Mar. 2, 1989; 3–D Coordinate Acquisition Software For the SAC GP8-3D Digitizer and the IBM Personal Computer; pp. 0–1—5–3.

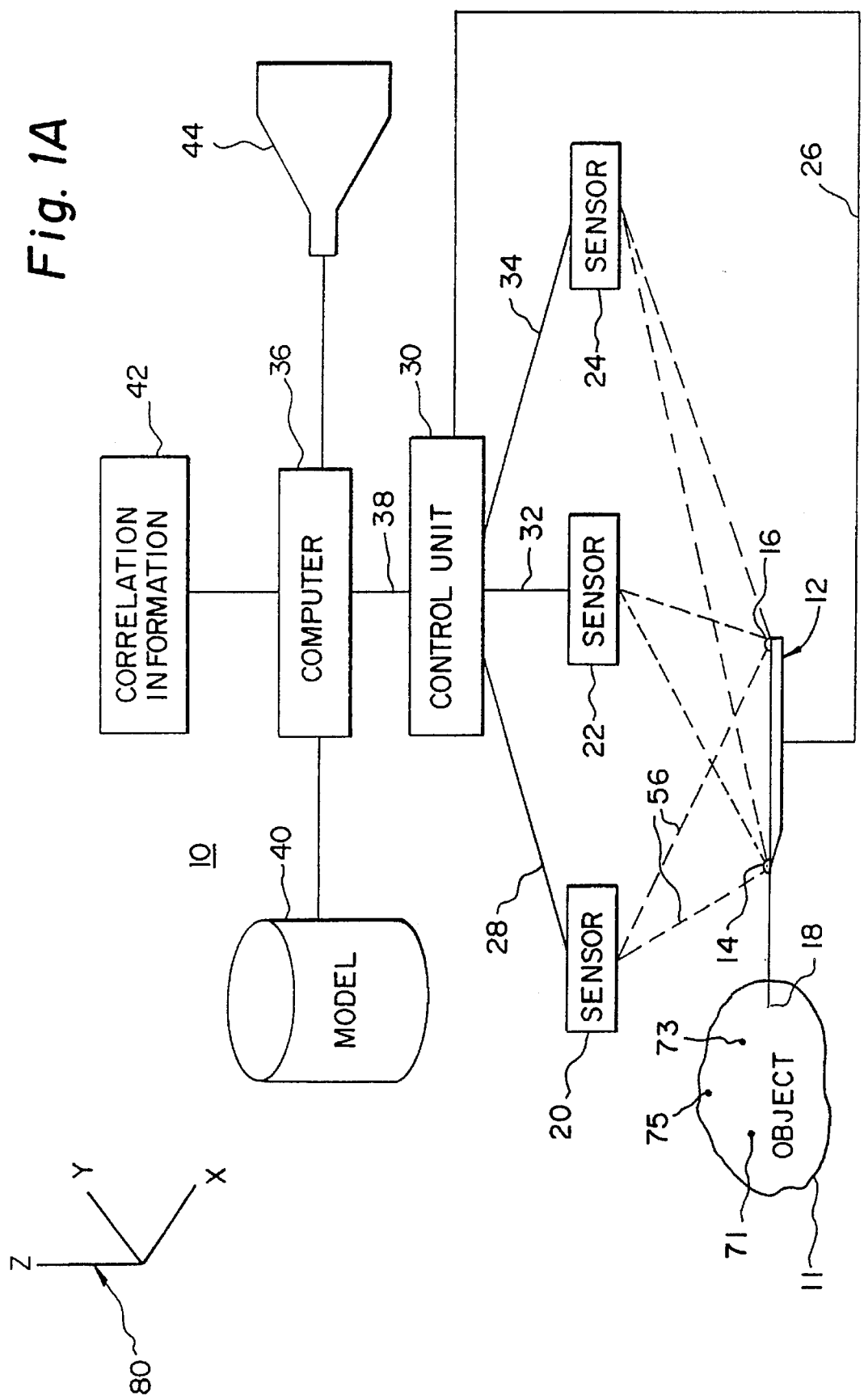

APPARATUS FOR DETERMINING THE POSITION AND ORIENTATION OF AN INVASIVE PORTION OF A PROBE INSIDE A THREE-DIMENSIONAL BODY

This is a continuation of U.S. Ser. No. 08/052,042, now abandoned which is a continuation-in-part of U.S. Ser. No. 07/909,097, U.S. Pat. No. 5,383,454, which is in turn a continuation-in-part of U.S. Ser. No. 07/600,753, now abandoned, the entire contents of which are incorporated herein by reference.

BACKGROUND OF THE INVENTION

1. Field of the Invention

This invention relates to an improved method and apparatus for determining, in real time, the position of the tip of an invasive probe inside a three-dimensional object and displaying its position relative to a geometrical model of that object visually displayed on a computer screen. More specifically, this invention relates to an improved method and apparatus of interactively determining the position of a probe tip inside the head of a patient during intracranial surgery relative to a three-dimensional internal diagnostic image of that patient.

2. Description of the Prior Art

Computed tomography (CT), magnetic resonance imaging (MRI), and other methods provide important detailed internal diagnostic images of human medical patients. However, during surgery there often is no obvious, clear-cut relationship between points of interest in the diagnostic images and the corresponding points on the actual patient. While anomalous tissue may be obviously distinct from normal healthy tissue in the images, the difference may not be as visible in the patient on the operating table. Furthermore, in intracranial surgery, the region of interest may not always be accessible to direct view. Thus, there exists a need for apparatus to help a surgeon relate locations in the diagnostic images to the corresponding locations in the actual anatomy and vice versa.

The related prior art can be divided into art which is similar to the present invention as a whole and art which is related to individual components of this invention.

Prior art similar to the present invention as a whole includes methods of correlating three-dimensional internal medical images of a patient with the corresponding actual physical locations on the patient in the operating room during surgery. U.S. Pat. No. 4,791,934 does describe a semi-automated system which does that, but it requires additional radiographic imaging in the operating room at the time of surgery as the means to correlate the coordinate systems of the diagnostic image and the live patient. Furthermore, the system uses a computer-driven robot arm to position a surgical tool. In particular, it does not display the location of an input probe positioned interactively by the surgeon.

There have been other attempts to solve the three-dimensional localization problem specifically for stereotactic surgery. One class of solutions has been a variety of mechanical frames, holders, or protractors for surgery (usually intracranial surgery). For examples see U.S. Pat. Nos. 4,931,056; 4,875,478; 4,841,967; 4,809,694; 4,805,615; 4,723,544; 4,706,665; 4,651,732; and 4,638,798. Generally, these patents are intended to reproduce angles derived from the analysis of internal images, and most require rigidly screwing a stereotactic frame to the skull. In any case, these methods are all inconvenient, time-consuming, and prone to human error.

A more interactive method uses undesirable fluoroscopy in the operating room to help guide surgical tools (U.S. Pat. No. 4,750,487).

More relevant prior art discloses a system built specifically for stereotactic surgery and is discussed in the following reference:

David W. Roberts, M.D., et al; "A Frameless Stereotaxic Integration of Computerized Tomographic Imaging and the Operating Microscope", *J. Neurosurgery* 65, October 1986.

It reports how a sonic three-dimensional digitizer was used to track the position and orientation of the field of view of a surgical microscope. Superimposed on the view in the microscope was the corresponding internal planar slice of a previously obtained computed tomographic (CT) image. The major disadvantages reported about this system were the inaccuracy and instability of the sonic mensuration apparatus.

Although the present invention does not comprise the imaging apparatus used to generate the internal three-dimensional image or model of the human patient or other object, the invention does input the data from such an apparatus. Such an imaging device might be a computed tomography (CT) or magnetic resonance (MRI) imager. The invention inputs the data in an electronic digital format from such an imager over a conventional communication network or through magnetic tape or disk media.

The following description concentrates on the prior art related specifically to the localizing device, which measures the position of the manual probe and which is a major component of this invention. Previous methods and devices have been utilized to sense the position of a probe or object in three-dimensional space, and employ one of various mensuration methods.

Numerous three-dimensional mensuration methods project a thin beam or a plane of light onto an object and optically sense where the light intersects the object. Examples of simple distance rangefinding devices using this general approach are described in U.S. Pat. Nos. 4,660,970; 4,701,049; 4,705,395; 4,709,156; 4,733,969; 4,743,770; 4,753,528; 4,761,072; 4,764,016; 4,782,239; and 4,825,091. Examples of inventions using a plane of light to sense an object's shape include U.S. Pat. Nos. 4,821,200, 4,701,047, 4,705,401, 4,737,032, 4,745,290, 4,794,262, 4,821,200, 4,743,771, and 4,822,163. In the latter, the accuracy of the surface sample points is usually limited by the typically low resolution of the two-dimensional sensors usually employed (currently about 1 part in 512 for a solid state video camera). Furthermore, these devices do not support the capability to detect the location and orientation of a manually held probe for identifying specific points. Additionally, because of line-of-sight limitations, these devices are generally useless for locating a point within recesses, which is necessary for intracranial surgery.

The internal imaging devices themselves (such as computed tomography, magnetic resonance, or ultrasonic imaging) are unsuited for tracking the spatial location of the manually held probe even though they are unencumbered by line-of-sight restrictions.

A few other methods and apparatus relate to the present invention. They track the position of one or more specific moveable points in three-dimensional space. The moveable points are generally represented by small radiating emitters which move relative to fixed position sensors. Some methods interchange the roles of the emitters and sensors. The typical forms of radiation are light (U.S. Pat. No. 4,836,778), sound (U.S. Pat. No. 3,821,469), and magnetic fields (U.S. Pat. No. 3,983,474). Other methods include clumsy mechanical arms or cables (U.S. Pat. No. 4,779,212). Some electro-optical approaches use a pair of video cameras plus a computer to calculate the position of homologous points in a pair of stereographic video images (for example, U.S. Pat. Nos. 4,836,778 and 4,829,373). The points of interest may be passive reflectors or flashing light emitters. The latter simplify finding, distinguishing, and calculating the points.

Probes with a pointing tip and sonic localizing emitters on them have been publicly marketed for several years. The present invention also utilizes a stylus, but it employs tiny light emitters, not sound emitters, and the method of sensing their positions is different.

Additional prior art related to this patent is found in these references:

Fuchs, H.; Duran, J.; Johnson, B.; "Acquisition and Modeling of Human Body Form Data", *Proc. SPIE*, vol. 166, 1978, pp. 94–102.

Mesqui, F.; Kaeser, F.; Fischer, P.; "Real-time, Non-invasive Recording and 3-D Display of the Functional Movements of an Arbitrary Mandible Point", *SPIE Biostereometrics*, Vol. 602, 1985, pp. 77–84.

Yamashita, Y.; Suzuki, N.; Oshima, M. "Three-Dimensional Stereometric Measurement System Using Optical Scanners, Cylindrical Lenses, and Line Sensors", *Proc. SPIE*, vol. 361, 1983, pp. 67–73.

The paper by Fuchs, et al., (1978) best describes the method used by the present invention to track the surgical probe in three-dimensional space. It is based on using three or more one-dimensional sensors, each comprising a cylindrical lens and a linear array of photodetectors such as a charge-coupled semiconductor device (CCD) or a differential-voltage position sensitive detector (PSD).

The sensors determine intersecting planes which all contain a single radiating light emitter. Calculation of the point of intersection of the planes gives the location of the emitter. The calculation is based on the locations, orientations, and other details concerning the one-dimensional sensors and is a straightforward application of analytic geometry. This electro-optical method, however, has not been previously used for the purpose of the present invention.

Thus, there still remains a need for a complete apparatus which provides fast, accurate, safe, convenient mensuration of the three-dimensional position of a manual probe and which visually relates that position to the corresponding position on the image of a previously-generated three-dimensional model of an object.

SUMMARY OF THE INVENTION

A first objective of the present invention is to provide accurate, three-dimensional mensuration of the location and orientation of an instrument on or inside an object, which could be (but is not limited to) a surgical patient in an operating room.

A second objective of this invention is to provide an electro-optical mensuration system which is inexpensive, easy to use, reliable, and portable and which employs a manually positioned probe or other pointing instrument.

A third objective of this invention is to provide a simple, non-invasive means of establishing a correspondence between a predetermined coordinate system of the object and a coordinate system of a three-dimensional, geometrical computer model of that object where the computer model has been provided as input data to this invention.

A fourth objective of this invention is to relate a measured location on or inside the object to the corresponding location in the computer model of that object according to the established correspondence between the coordinate systems of the object and the model.

A fifth objective of this invention is to display a cut-away view or a cross-sectional slice of that model on the graphics screen of the invention, where the slice may be a planar cross-section of the geometrical model, where the slice approximately intersects the location in the model corresponding to the measured location. A marker may then be superimposed on the displaced slice to indicate the location on the slice corresponding to the measured location.

A sixth objective of this invention, is specifically to help a surgeon locate diseased tissue while avoiding healthy critical structures, especially in cranial neurosurgery.

Additional objects, advantages, and novel features of the invention shall be set forth in part in the following description and in part will become apparent to those skilled in the art upon examination of the following or may be learned by the practice of the invention. The objects and the advantages of the invention may be realized and attained by means of the instrumentalities and in combinations particularly pointed out in the appended claims.

To achieve the foregoing and other objects and in accordance with the invention, as embodied and broadly described herein, the optical mensuration and correlation apparatus comprises a hand held probe having an invasive tip for touching or for inserting into an object. Two or more light emitters mounted in spaced relation to each other on the external portion of the probe remaining outside the object are sequentially strobed to emit light. Three or more light sensors or detectors, the positions of which are known with respect to a predetermined coordinate system, detect the positions of the two or more light emitters positioned on the probe as they are strobed. A computer-coupled to the probe and to the light sensors receives data from the sensors and calculates the position and orientation of the probe, with respect to the predetermined coordinate system. The computer then determines the position and orientation of the invasive portion of the probe inside the object by correlating the position of the invasive portion of the probe relative to the predetermined coordinate system with a model of the object defined relative to the predetermined coordinate system. A display device coupled to the computer indicates the location of the invasive portion of the probe in the object by displaying a representation of the location of the invasive portion of the probe with respect to the model of the object.

The method of this invention includes the steps of detecting the position of the probe relative to the predetermined coordinate system, computing the position and orientation of the invasive portion of the probe relative to the predetermined coordinate system, determining the position and orientation of the invasive portion of the probe inside the object by correlating the position of the invasive portion of the probe relative to the predetermined coordinate system with the model of the object, and indicating the location of the invasive portion of the probe in the object by displaying a representation of the location of the invasive portion of the probe with respect to the model of the object.

BRIEF DESCRIPTION OF THE DRAWINGS

The accompanying drawing figures, illustrate a preferred embodiment of the present invention and, together with the description, serve to explain the principles of the invention.

FIG. 1A–B are block diagrams of the optical mensuration and correlation apparatus of the present invention showing the major components.

DETAILED DESCRIPTION OF THE PREFERRED EMBODIMENT

Figure 1B:
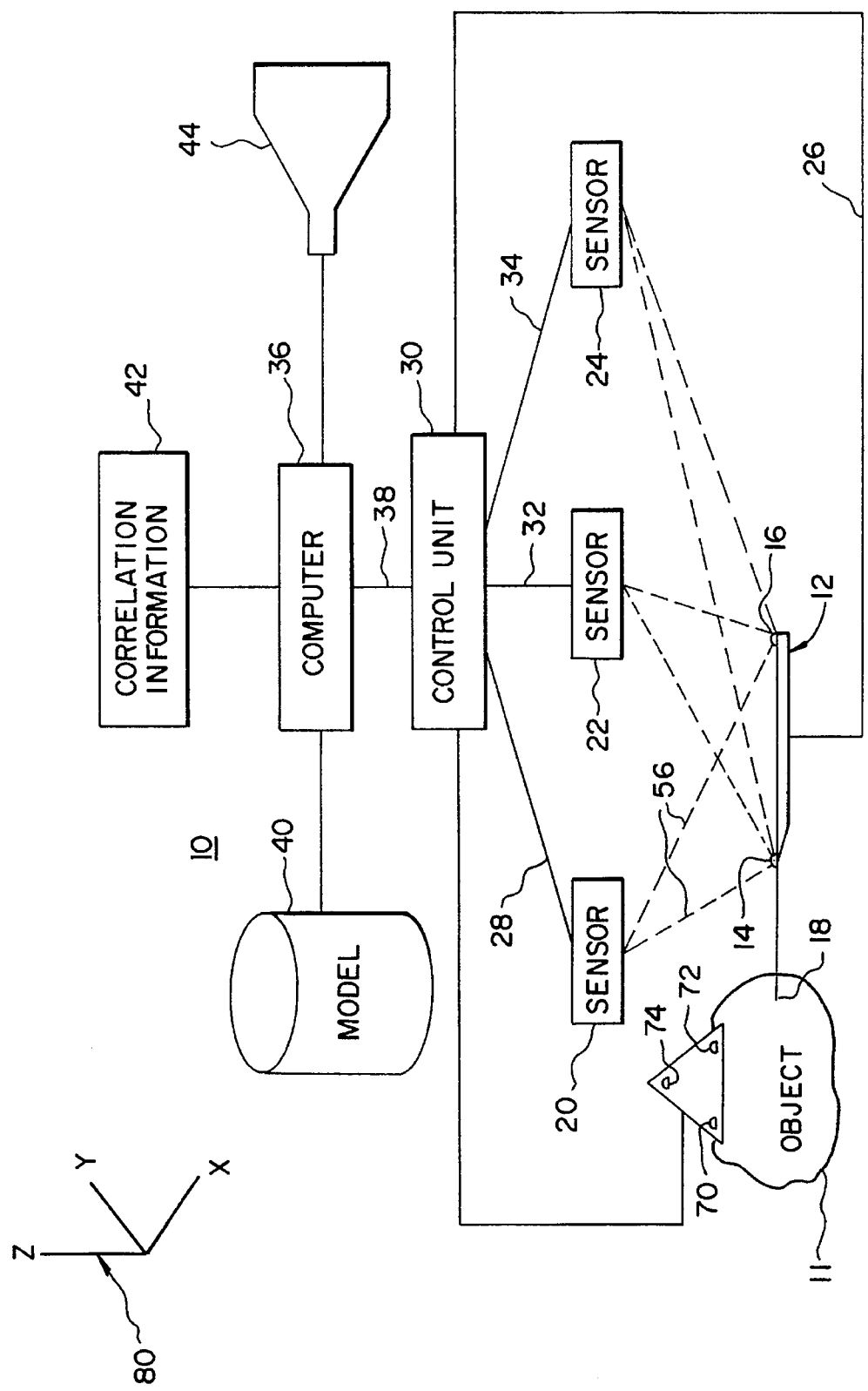

The optical mensuration and correlation apparatus 10 of the present invention is shown schematically in FIGS. 1A–B and comprises a hand-held invasive probe 12 housing at least two light emitters 14, 16, mounted co-linear with one another and with the tip 18 of the probe 12. At least thee remotely located, one-dimensional light energy sensors 20, 22, and 24 are mounted in fixed, spaced relationship to each other and are located at known positions and orientations with respect to a predetermined reference coordinate system frame 80. Three light sensors 20, 22, and 24 sense the light projected by the individual light emitters 14, 16 and generate electrical output signals from which are derived the location of the probe 12 and, consequently, the probe tip 18, with respect to the fixed coordinate system 80. In addition, the three sensors 20, 22, 24 could sense and derive the locations of other, optional reference emitters 70, 72 and 74 (FIG. 1B) in the same manner for the probe emitters 14 and 16. The role of these reference emitters is to automate the calculation of the transformation matrix between the coordinate system of the model's image 13 (FIG. 2) of the object and the coordinate system of the sensors and the object itself 11.

A control unit 30 connected to the moveable probe 12 via a data line 26 and coupled to the remotely located sensors 20, 22, and 24 via data lines 28, 32, and 34, respectively, synchronizes the time multiplexing of the two light emitters 14, 15, controls the operation of the sensors 20, 22, and 24, and receives data from these sensors as will be completely described below. A coordinate computer 36, coupled to the control unit 30 by a data line 38, calculates the three-dimensional spatial positions of the probe 12 and the probe 18, and correlates those positions with data from a model 13 of the object 11 which has been previously stored electronically in an electronically accessible database 40 and from correlation information 42. Finally, the computer 36 displays a representation 76 of the position of the probe tip 18 with respect to the computer image 13 of the object 11 on display screen 44 (FIG. 2) as will be fully described below.

The probe 12 can be used without the cable 26 coupling it to the control unit 30 by employing distinctive modulation of the light emitters 14 and 16. For example, the pulse durations or frequencies of each can be different. The controller 30, by detecting the pulse duration or frequency, can determine to which light emitter the sensors 20, 22, and 24 are reacting.

The optical mensuration and correlation apparatus 10 of the present invention is primarily designed to aid surgeons performing delicate intracranial surgery, and the remaining description is directed to such a surgical embodiment although many other surgical applications besides cranial surgery are possible. Moreover, the optical mensuration and correlation apparatus 10 of this invention may be used for other purposes in many various non-medical fields. In the described embodiment, the physical object 13 of interest is the head or cranium of a patient, and the model of the cranium is constructed using a series of parallel internal image slices (of known mutual spatial relationship) such as those obtained by means of computed tomography (CT) or nuclear magnetic resonance (NMR). These image slices are then digitized, forming a three-dimensional computer model of the patient's cranium which is then stored in the electronically accessible database 40.

As shown in FIGS. 1A, 1B, 2, and 3 a surgeon places the tip 18 of the probe 12 at any point on or inside the cranium 11 of the patient. The position sensors 20, 22, and 24 detect the locations of the emitters 14, 16 attached to the portion of the probe 12 that remains outside the patient's body. That is, the light produced by the emitters 14, 16 must be visible to the sensors 20, 22, and 24. These point emitters 14, 16 radiate light through a wide angle so that they are visible at the sensors over a wide range of probe orientations.

Figure 2:
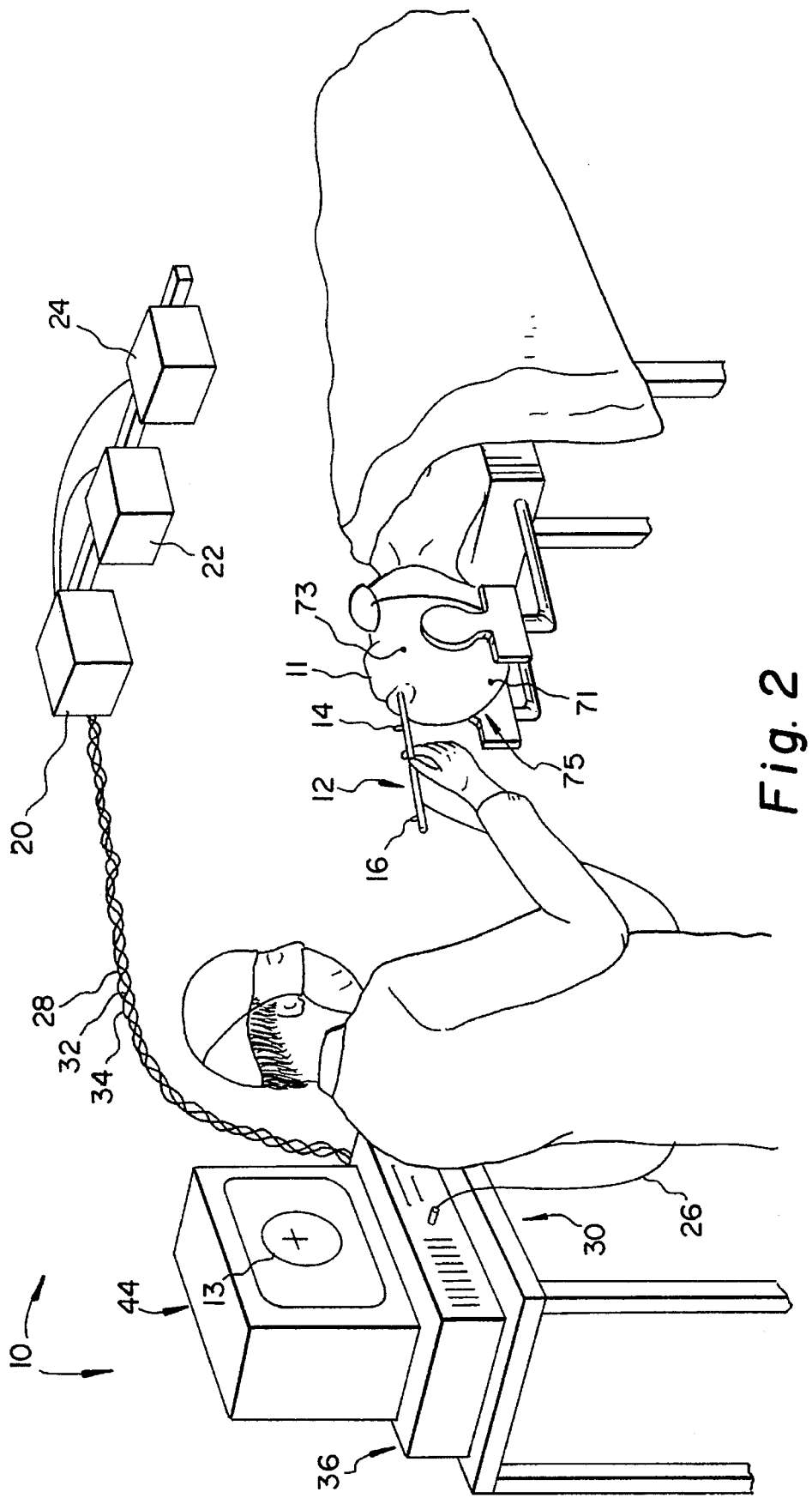
FIG. 2 is a perspective drawing illustrating the invention in use by a surgeon performing intracranial surgery on a patient, and showing a cursor on the display screen that marks the corresponding position of the invasive tip of the probe within the image of previously obtained model data.
Figure 3:
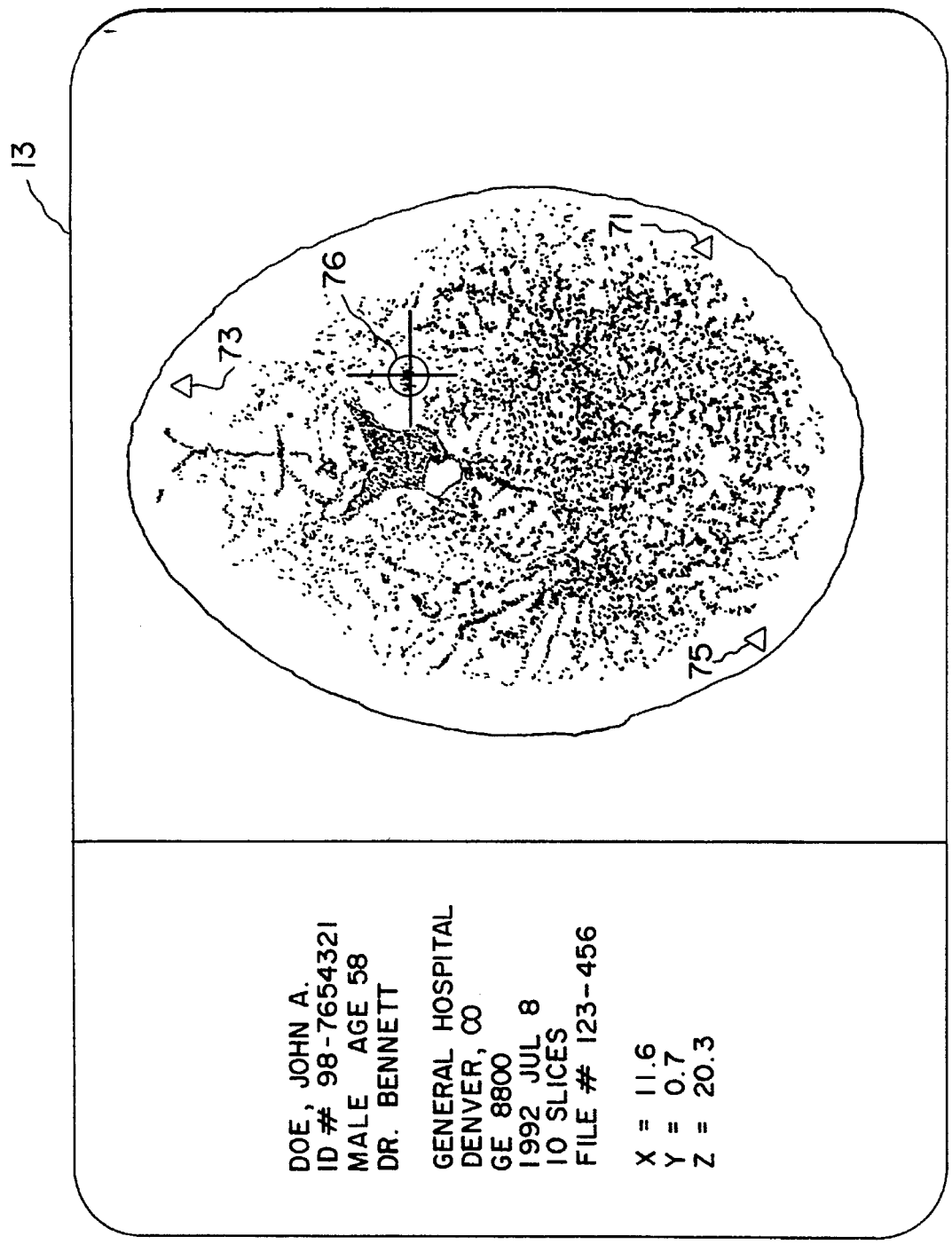
FIG. 3 is a sample of the display showing a position of tip of the probe with respect to previously obtained model data and showing the reference points on the patient's skull display as triangles.

The sensors 20, 22, and 24, the control unit 30, and the computer 36 determine the three-dimensional location of each emitter 14, 16, and compute its coordinates in the predetermined coordinate system 80. The computer 36 can then calculate the location of the tip 18 of the probe 12 with respect to the predetermined coordinate system 80, according to the locations of the emitters with respect to the predetermined coordinate system 80 and the dimensions of the probe, which dimensions had been placed into the memory (not shown) of the computer 36 beforehand as will be described fully below. Once the computer 36 has calculated the location of the probe tip 18 with respect to the predetermined coordinate system 80, the computer 36 then uses the relationship between the model of the cranium stored in the database 40 and the coordinate system 80 to calculate the location of the probe tip 18 in relation to the model 11. Finally, the computer 36 displays the model-relative location 76 of the tip 18 on an display screen 44. In a simple form of the preferred embodiment, the computer 36 accomplishes this display by accessing a CT or NMR image slice 13 stored in the database 40 that is closest to the location of the probe tip 18, and then superimposes a suitable icon 76 representing the tip 18 on the image 13 as shown in FIGS. 2 and 3. Thus, the surgeon knows the precise location of the probe tip 18 in the patient's cranium relative to the image data by merely observing the display screen 44. An advanced form of the present invention could derive and display an arbitrary oblique cross-section through the multiple image slices, where the cross-section is perpendicular to the probe direction.

Figure 4:
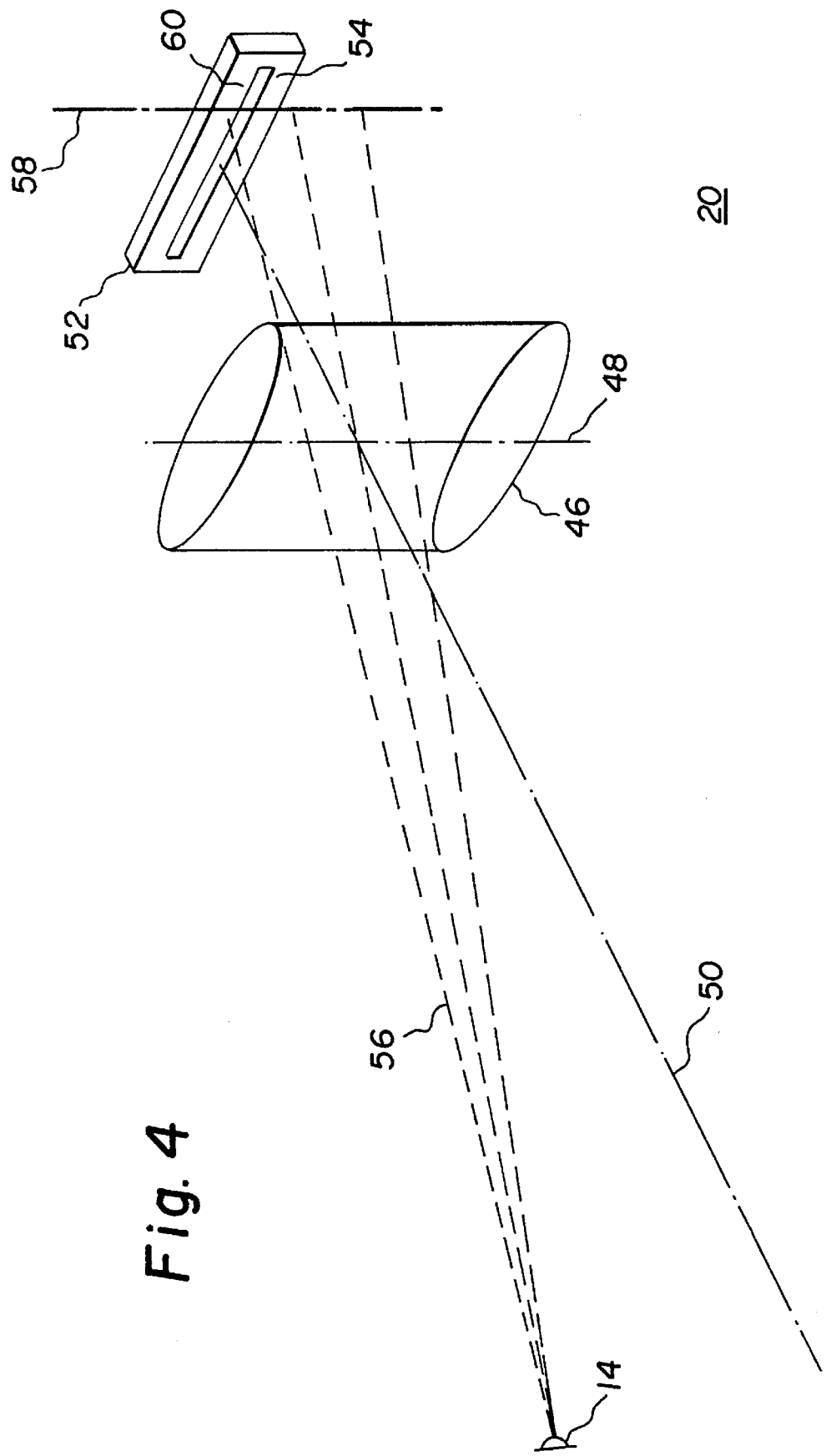
FIG. 4 is a schematic perspective representation of one of the one-dimensional photodetectors of the present invention.

The details of the optical mensuration and correlation apparatus 10 of the present invention are best understood by reference to FIGS. 1 and 4 collectively. Essentially, the probe 12 houses the two light emitters 14, 16, which are rigidly attached to the probe 12. Since only two emitters are used, the emitters 14, 16 must be collinear with the tip 18 of the probe 12 so that the computer 36 can determine uniquely the position of the tip 18 in three dimensions. Moreover, for reasonable measurement accuracy, the emitters 14, 16 should be at least as far from each other as they are from the tip 18. In any case, the geometrical relationship of the emitters 14, 16 to each other and to the probe tip 18 should be specified to the computer 36 beforehand so that the computer 36 can compute the exact location and orientation of the tip 18 based on the locations of the individual light emitters 14, 16. The use of three emitters does not require that the probe tip be colinear with the emitters. Three or more emitters provides full orientation information. Although the invention is described as showing only a cursor as locating the relative position of the probe tip 18, the invention can be modified to display a line or shaped graphic to indicate the location of the points of all of the inserted portion of the probe. This would entail only the determination of additional points along the probe.

The two light emitters 14, 16 can be high intensity light emitting diodes (LEDs), which are preferably time multiplexed or strobed by control unit 30 in a predetermined manner such that only one light emitter LED is "on" or emitting light at any one time as will be described in more detail below. The light emitted from any one of these emitters 14, 16 is detected by each of the three emitter sensors 20, 22, and 24, which then determine the position of each particular emitter in relation to the known positions of the detectors 20, 22, and 24 at the time it is strobed or illuminated.

Each of the one-dimensional sensors 20, 22, and 24 used in the preferred embodiment 10 of the present invention are identical to one another in every respect. Therefore, for the purpose of giving a detailed description of this embodiment, only the sensor 20 is shown and described in detail, since the remaining sensors 22 and 24 are identical.

In FIG. 4, a one-dimensional sensor 20 comprises a cylindrical lens 46 having a longitudinal axis 48 which is orthogonal to the optical axis 50 of the sensor 20. A linear photodetector 52, such as a charge coupled device (CCD) with several thousand elements or a similar device capable of linear light detection with an elongated aperture 54, is positioned in such a manner that the optical axis 50 passes through the aperture 54 and such that the long axis of the aperture 54 is orthogonal to the longitudinal axis 48 of the lens 46. Light beams 56 from the emitters 14, 16 are focused by the cylindrical lens 46 into a real image line 58 on the surface 60 of linear photodetector 52.

The photodetector 52 then generates an output 68 (FIG. 5) that is related to the position of real image line 58 on the surface 60 of photodetector 52, thus characterizing the location of the image itself. That is those elements of the detector 52 illuminated by the real image line 58 will generate a strong signal while those not illuminated will generate none or very small signals. Thus, a graph of image intensity (or signal strength) versus location on the surface of the photodetector will resemble the signal peak curve 68 shown in FIG. 5. The "all-emitters-off" (or background), signal level 66 is never quite zero due to the effects of environmental light, electronic noise, and imperfections in the sensor. In any event, since the image of the illuminated emitter is focused into line 58, only the horizontal displacement of emitter 14 from optical axis 50 is measured by detector 52, hence the designation "one-dimensional detector."

Thus, a single one-dimensional detector 20 can only locate the plane on which an illuminated emitter 14 lies, and the detector 20 cannot, by itself, determine the unique point in space at which illuminated emitter 14 is located. To precisely locate the location in space of the illuminated emitter 14 requires three such detectors positioned in spaced relationship to each other since the intersection of three planes are required to define a point.

To locate the position of a particular illuminated one of emitters 14, 16, the light sensors 20, 22, and 24 are mounted so that their optical axes are not all parallel. In the preferred embodiment, two light sensors, such as sensors 20, 24 in FIG. 2, are situated so that their respective axes 48 (FIG. 4) are in parallel spaced relationship with the third detector 22 situated between the other two but with its axis 48 perpendicular to the axes of the other two. That is, the sensors 20, 22, and 24 should be arranged along a line or arc (FIG. 2), such that each sensor 20, 22, and 24 is generally equidistant from the center of the volume in which the measurements are made equally spaced, and all aimed at the center of the measurement volume. If the sensors 20, 22, and 24 are arranged along such a horizontal arc, then the middle sensor should be oriented so as to measure the angular elevation of the light emitters as described above. The two outer sensors, therefore, measure the horizontal angle (azimuth) relative to themselves. Data from the outer sensors are used to stereographically calculate both horizontal position and distance from the sensors as will be described below.

The accuracy of three-dimensional measurements depends on the angle formed between the outer two sensors 20 and 24, where the emitter to be measured is at the vertex of the angle. Accuracy improves as that angle approaches a right angle. All three sensors 20, 22, and 24 must be spaced so that the desired measurement volume is completely within their field of view which can be accomplished by making the focal length of the lens 46 short enough to provide coverage of the desired field of view. Alternatively, additional sensors, identical to sensors 20, 22, and 24, could be used either to broaden coverage of the field of view or to enhance measurement resolution.

While this process of detecting the position of a given illuminated emitter 14, 16 can locate the exact position of the illuminated emitter, it cannot by itself determine the particular orientation and location of the probe tip 18 in three-dimensional space. To do so with only two emitters requires that both emitters 14, 16 be collinear with the probe tip 18, as described above. Also, the distances between each emitter 14 and 16, (as well as the distances between the emitters 14, 16) and the probe tip 18 must be known and loaded into the memory of the computer 36 before the computer 36 can determine the location of the probe tip 18 from the locations of the emitters 14, 16. Consequently, when each of the emitters 14, 16 are rapidly turned on in sequence, or strobed, while the probe is held relatively stationary, the sensors 20, 22, and 24 can detect the exact position of each emitter in turn. Thus computer 36 can determine the exact location and orientation of the probe tip 18. Since only one of the emitters 14, 16 is on at any one time, the detectors 20, 22, and 24 locate the position of that particular illuminated emitter only. If the strobe rate, that is, the frequency at which the emitters 14, 16 are turned on and off in sequence, is fast enough, the detectors 20, 22, and 24 can, for all practical purposes, determine the position and orientation of the probe tip 18 at any instant in time.

The detectors or sensors 20, 22, and 24 need only distinguish which of the light emitters 14, 16 is "on" or illuminated at any one time. In the preferred embodiment 10 of the present invention, this function is accomplished by strobing or illuminating each of the emitters 14, 16 in sequence, as described above. However, other methods could be used to allow the detectors or sensors 20, 22, and 24 to distinguish the respective pilot light emitters 14, 16 from one another. For example, different colors of light could be used in conjunction with detectors capable of distinguishing those particular colors or wavelengths of light. Alternatively, the respective light emitters 14, 16 could be modulated with a unique "tone" for each emitter. The control unit 30 or computer 36 could then be programmed to demodulate the tone, to determine to which particular emitter 14 or 16 the position signal belongs. Numerous other methods of distinguishing the light emitters 14 and 16 are possible and would be readily apparent to persons having ordinary skill in the art. Therefore, the present invention should not be regarded as limited to the particular strobing method shown and described herein.

Auto-focusing or multiple-lens optics may be integrated into the sensors 20, 22, and 24 to improve the performance of the system. However, the simple, fixed-focus optics shown and described herein and in FIG. 4 for one sensor provide a good level of performance if the focal length of the lenses 46 are kept short and if the working range of the probe 12 is restricted. Even if the real image of a light emitter 14 or 16 is somewhat out of focus on the photodetector 52, the angular measurement of the image is still usable. A useable measurement for each of the sensors 20, 22, or 24 to generate could be any of the following: (1) the position of the photodetector element with peak intensity, (2) the intensity-weighted average of all overthreshold elements, or simply (3) the average of the minimum and maximum elements where the intensity is over some threshold as will be completely described below. The photodetector 52 should be placed at the focus for the farthest typical operating distance of the light emitters. Closer emitters will form slightly de-focused images 58, but they require less precise angular measurement for a given distance accuracy. Furthermore, their de-focused real images are brighter, which increases the brightness gradient at the edges of the image.

As described so far, the real image 58 of the currently activated emitter must be significantly brighter than the rest of the light falling on the photodetector 52. Otherwise, other lights or reflective surfaces in the field of view of the sensors will hinder the detection of the emitter's real image. Therefore, it is desirable to include in the apparatus circuitry to subtract the background light focused on the photodetectors as will be described in detail below. This circuitry enhances use of the invention where the sensors are to detect the light emitters against relatively bright backgrounds. While the light emitters are all momentarily extinguished, the one-dimensional data from each sensor are saved in a memory. This could be done in an analog delay line or by digitally sampling the output signal and storing it in a digital memory. Then, as each emitter is turned on sequentially, the saved data are subtracted from the current data generated by the illuminated emitter. If the background data are stored digitally, the new data is also digitized, and the stored background data is digitally subtracted from the new data.

Figure 5:
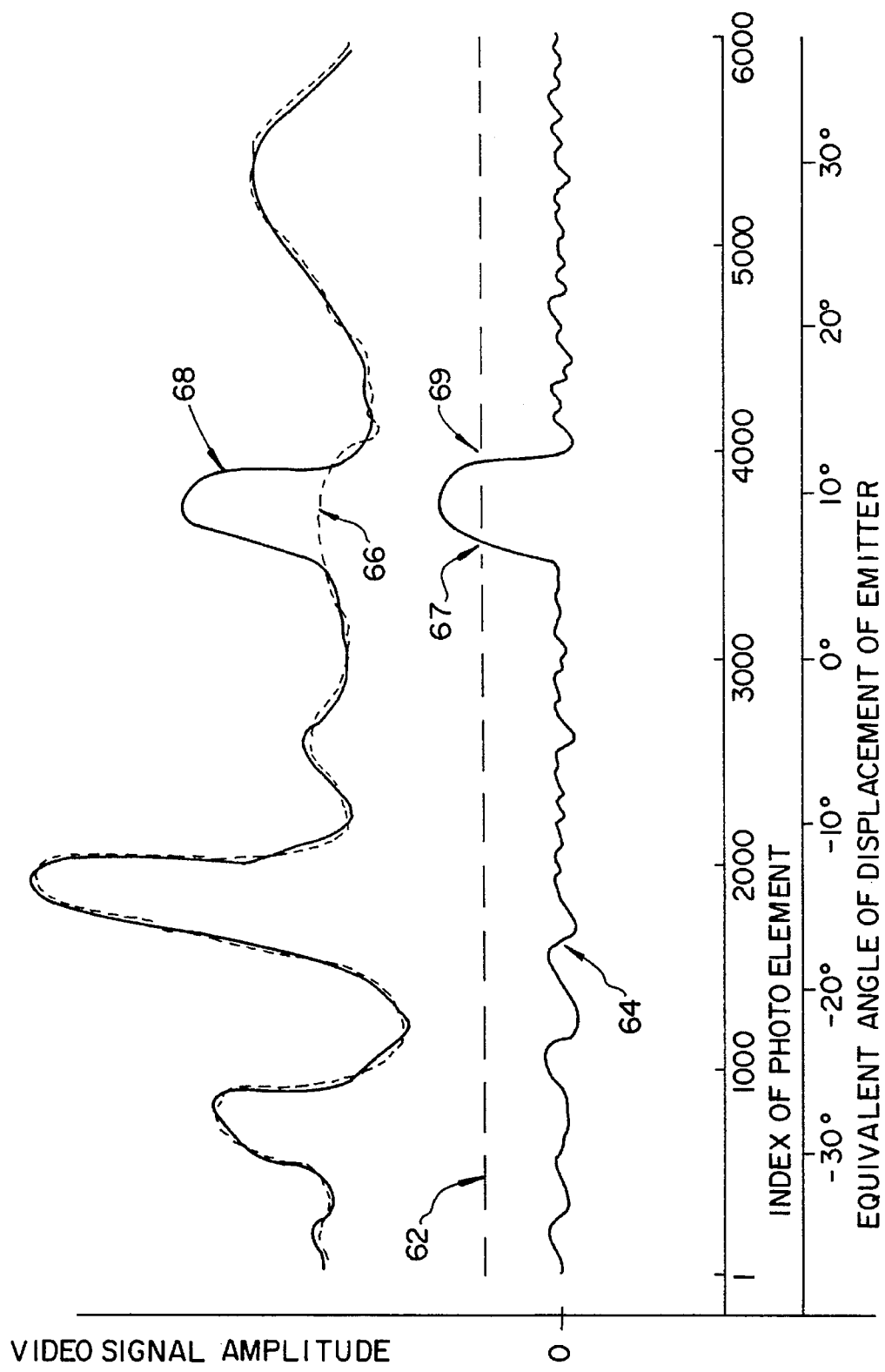
FIG. 5 is a graph of the image intensity (manifested as a voltage or current) versus locations on the photodetector surface for a typical light detector used by the optical mensuration and correlation apparatus of the present invention.

A graphical representation of the light intensity of the image, or equivalently, the generated output voltage amplitude for each element in the row of photodetector elements, is shown in FIG. 5. The graph depicts typical background image intensities 66 with all emitters off, the intensities 68 with one light emitter on, and the element-by-element difference 64 between the intensities with the emitter off and those with it on. The measurements will likely contain some random electronic noise, and two consecutive measurements for a given photodetector element may differ slightly even where the background is unchanged. Therefore, the differential intensities 65 between two consecutive measurements 66, 68 also contain some random electronic noise. However, the two measurements differ substantially only at the location of the light emitter image, and this difference exceeds the threshold level 62.

Figure 6:
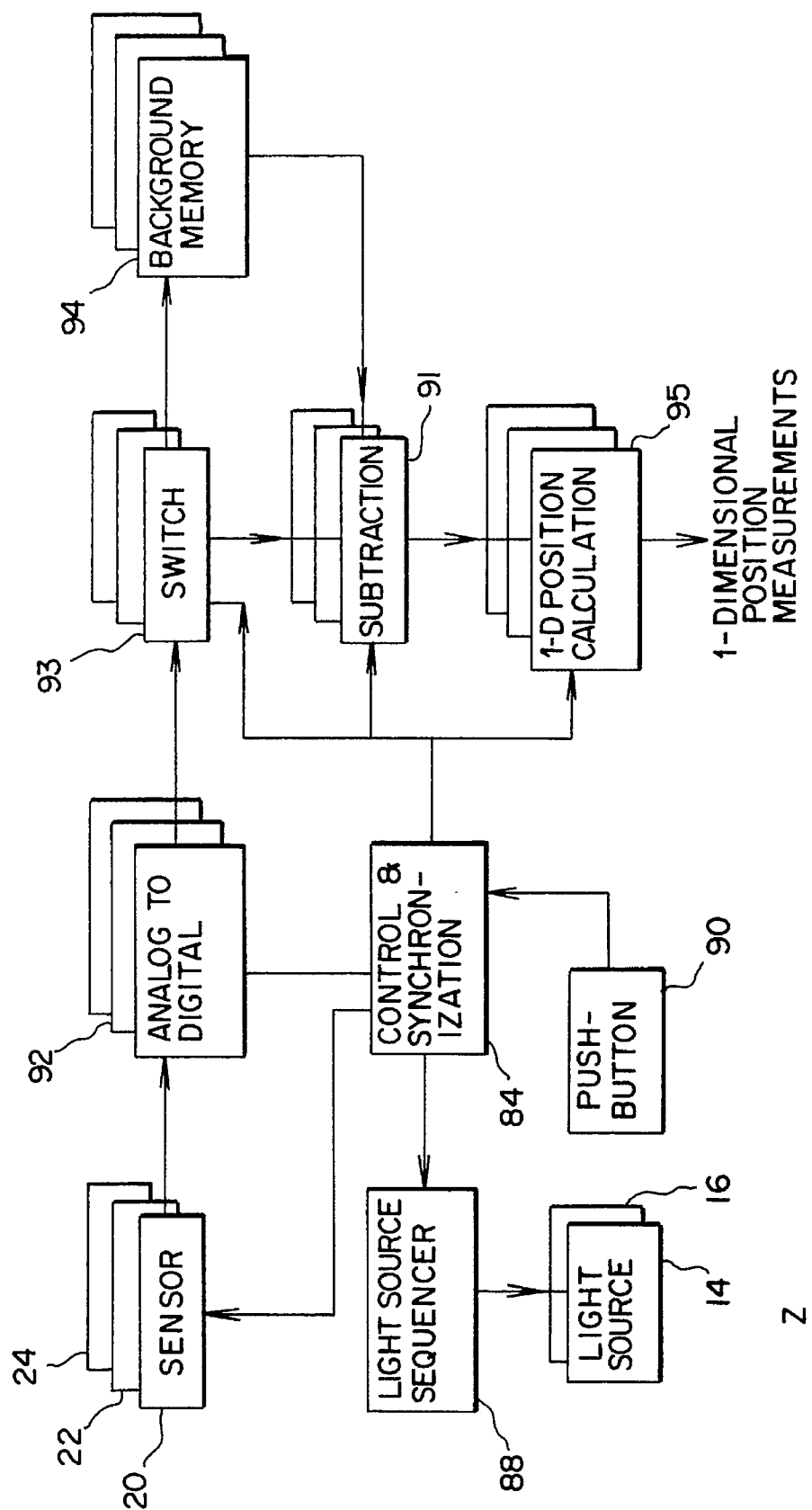
FIGS. 6 and 7 are diagrams of the major steps performed by the computer to calculate the position of the invasive portion of the probe with respect to the model of the object and to display the image slice.

The details of the structure and operation of the control unit 30 are best seen in FIG. 6. Specifically, control unit 30 (FIG. 1) supplies power to the light emitters 14, 16, and the light sensors 20, 22, and 24. A control and synchronization unit 84 and light source sequencer 88 time-multiplexes or strobes the emitter lights 14, 16 individually, as described above, so that the position and orientation of the probe tip 18 (FIG. 1) can be determined from the signals received from the light sensors 20, 22, and 24. The angular data signals received from the light sensors 20, 22, and 24 are converted by an analog-to-digital converter 92. Actually, three analog-to-digital converters are used, as shown in FIG. 6, but only one is labeled and described herein for brevity since the other two analog-to-digital converters are identical and are used to convert the signals from the sensors 22 and 24.

The control and synchronization unit 84 also controls three switches, of which switch 93 is typical, which store all digital data received from the sensors 20, 22, and 24 when the light emitters 14, 16 are off and stores these data in a background memory 94. Then, when the light emitters 14, 16 are illuminated in sequence by light source sequencer 18, the control and synchronization unit 84 changes the state of switch 93 which then redirects the data from the three sensors 20, 22, and 24 to a subtraction unit 91. The subtraction unit 91 subtracts the background data from the illuminated data, thus resulting in a signal relatively free from the background noise signal 66 (FIG. 5) since it has been subtracted from the signal.

As shown in FIG. 6 in conjunction with FIG. 5, a 1-D (one-dimensional) position calculation unit 95 determines the location of the real image line 58 on the CCD sensor 52 (FIG. 4) by measuring the locations of the edges 67, 69 of the signal blip 68 (FIG. 5) generated by the CCD sensor based on a predetermined threshold signal level 62. The 1-D position calculation unit 95 then averages the distance between the two edges to find the center of the signal peak as shown in FIG. 5. This method of determining the center of the signal peak is well shown in the art and need not be described in further detail. Moreover, numerous other methods of determining the location of the signal peak or its centroid are known in the art and will be obvious to those of ordinary skill in the art. The method used depends on the signal characteristics of the light sensor used as well as the characteristics of the lens system used to focus the light onto the surface of the detector, in addition to other parameters. Those practicing this invention with the various alternates described herein would have no trouble selecting a signal detection algorithm best suited to the particular characteristics of the sensors.

Finally, control unit 30 (FIG. 1) transmits the position data to the computer 36. That is when the computer 36 is ready to compute the current location of the illuminated emitter 14 or 16 on the probe 12, the latest angular data from all sensors 20, 22, and 24 are provided for analyzation. If the sensors generate data faster than the control unit 30 can process them, the unprocessed angular data are simply discarded.

Figure 7:
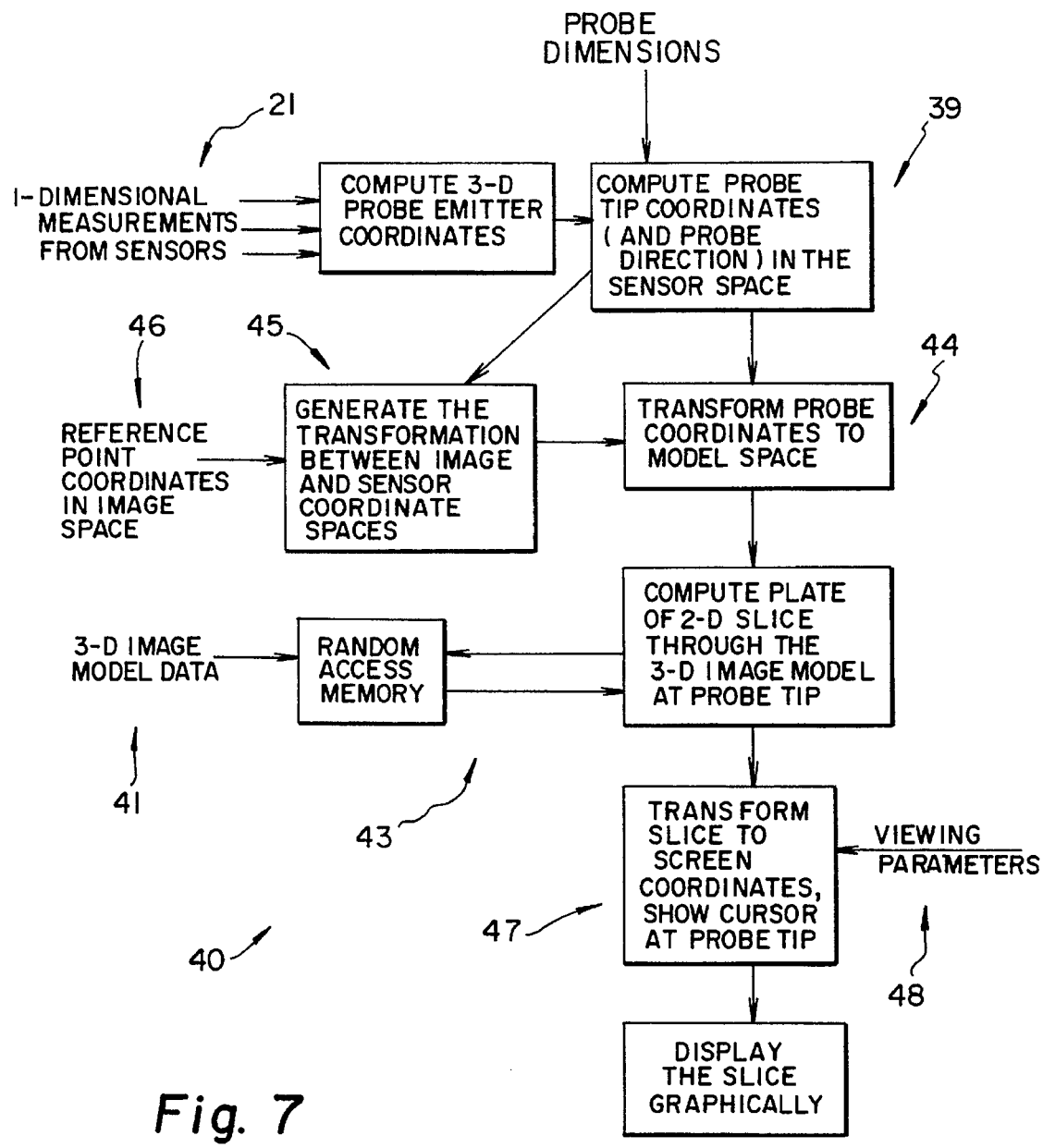

The operation of the computer 36 is most advantageously set forth in FIG. 7. The computer 36 calculates one-dimensional positions for each light emitter 14, 16, based on the location of the signal peak from each respective sensor 20, 22, and 24. These one-dimensional position signals are then used to determine the three-dimensional spatial coordinates of the emitters 14, 16, and thus for the probe 12 relative to the predetermined coordinate system 80 by coordinate transformation methods which are well-known in the art. The output signals from the computer 36 can be in any form desired by the operator or required by the application system, such as XYZ coordinate triples based upon some predetermined stationary rectangular coordinate system 80.

Figure 8:
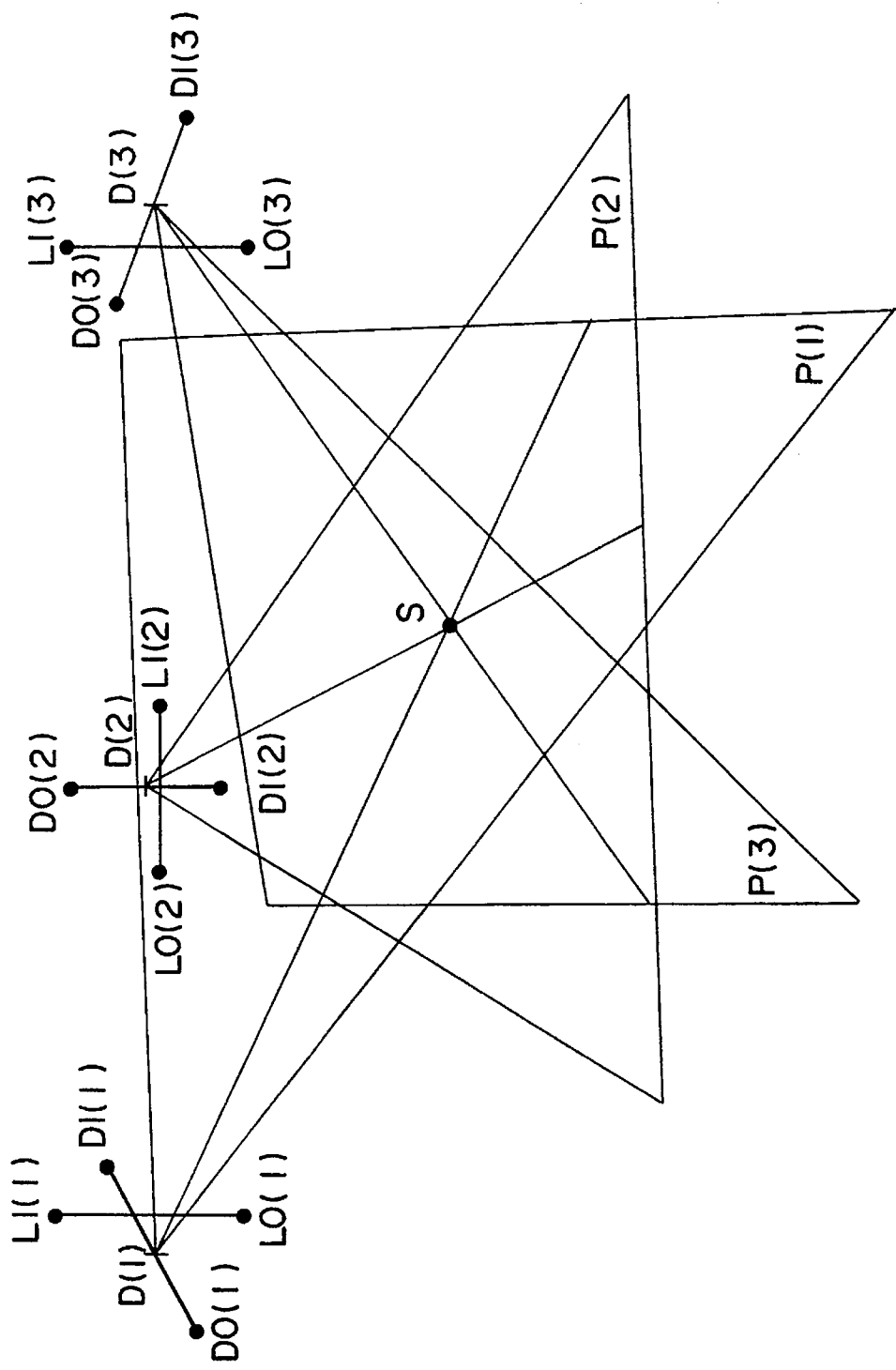
FIG. 8 is an illustration of the manner in which the three one-dimensional measurements determine three intersecting planes intersecting at a uniquely determined point.

FIG. 8 and the following paragraphs describe in detail how the position of a single light emitter 14, 16 is determined from the data returned from the sensors 20, 22, and 24. The following description applies to these three sensors 20, 22, and 24 only. If there are more than three such sensors, the calculation can be performed using any three of the sensors. Furthermore, if more than three sensors are used, the average of the points calculated from all combinations of three sensors could be used to increase accuracy. Another option is to use the point calculated from the three sensors closest to the light emitters 14, 16. The following parameters are considered to be known:

DO[i], one endpoint of each linear photodetector i;

Dl[i], the other endpoint of linear photodetector i;

LO[i], one endpoint of the axis of each lens i; and

Ll[i], the other endpoint of the axis of lens i.

T[i], a parametric value between 0 and 1 indicating where the peak or center of the line image of the emitter intersects the line segment between DO[i] and Dl[i] is The coordinates of point S are to be calculated, where S is the location of the light emitter.

For a CCD photodetector array, T[i] is the index of the element on which the center or peak of the image falls divided by the number of elements on the photodetector array, where i=1,2,3, . . . n, which is a number of sensors being used.

The three-dimensional coordinates of the above points are all referenced to a predetermined coordinate system 80. The cylindrical lens and linear photodetector do not directly measure an angle A of the light emitter about its lens axis; rather, they measure a value T[i] linearly related to the tangent of that angle by $$\tan(A) = C * (2*T[i]-1),$$

where C is a constant of proportionality that is related to and determined empirically by, the dimensions of a particular system.

The three-dimensional location where the image line intersects the linear photodetector is $$D[i]=(1-T[i])*DO[i]+(T[i])*Dl[i]$$

If the lens is ideal, then S also lies in plane P[i]. In reality, the point D[i] might have to be computed by a non-linear function F(t) that corrects for non-linear aberrations of the lens or the photodetector:

$$D[i]=(1-F(T[i]))*DO[i]+(F(T[i]))*Dl[i]$$

Function F(t) could be a polynomial in variable T, or it could be a value interpolated from an empirically determined table.

P[i] is a unique plane determined by the three points D[i], LO[i], and Ll[i], which are never collinear. S is the point of intersection of the planes P[1], P[2], and P[3] determined by sensors 20, 22, and 24. S is a unique point if at least two sensor lens axes are not parallel and if no two lens axes are collinear. The intersection point is found by finding the common solution S of the three equations defining the planes P[i]. Once the location S of each of the probe's light emitters is computed, the location of the probe's tip 18 can be calculated. The method of making such a determination is well known using the teaching of analytic geometry and matrix manipulations.

If M is a linear transformation matrix describing the relationship between a point R in the model space and a point S in the sensor space, then $$R*M=S.$$

If M' is the inverse of M and if S is a point in the sensor space, then the point in the model space corresponding to S is $$S*M'=R.$$

The preliminary steps required before practicing the method of the invention are now described. Then, after fully describing these preliminary steps, the detailed steps of the method of the optical mensuration and correlation apparatus are described.

Use of the invention takes place in three phases: the imaging phase; the correlation phase; and the normal operational phase. The imaging phase precedes the normal operation of the present invention. During the imaging phase, the body of the object of interest is used to build a three-dimensional geometrical model. In the preceding description, the object was the head of a human intracranial surgical patient because the invention is advantageously used in stereotactic neurosurgery. Accordingly, the three-dimensional model may comprise digital data from a series of internal cross-sectional images obtained from computed tomography (CT), magnetic resonance (MR), ultrasound, or some other diagnostic medical scanner. In any case, the image data stored in a suitable, electronic memory 40 which can be accessed later by the computer 36. The data is considered to be stored as a series of parallel two-dimensional rectangular arrays of picture elements (pixels), each pixel being an integer representing relative density. If the object is relatively rigid like a human head, this three-dimensional model may be created before the correlation and operational phases of the invention and possibly at another location.

Also, during the imaging phase, at least three non-collinear reference points 71, 73, and 75 (FIGS. 1A, 2 and 3), must be identified relative to the object 11. These may be represented by ink spots, tatoos, radiopaque beads, well-defined rigid anatomical landmarks, locations on a stereotactic frame, sterile pins temporarily inserted into rigid tissue or bone of a surgical patient, or some other reference means. The coordinates of these reference points are measured and recorded relative to the coordinate system of the imaging device. One way to accomplish this is to capture the reference points as part of the three dimensional model itself. For example, radiopaque pins could be placed within the image planes of diagnostic CT slices; the pin locations, if not automatically detectable because of their high density, can be identified interactively by the surgeon using a cursor on the computer display of the CT slices. See FIG. 3.

The correlation mode immediately precedes the normal operational phase of the present invention and must take place in the operating room. During the correlation phase, the invention accesses the data of the three-dimensional geometrical model of the patient, including the reference point coordinates which were recorded earlier. Next the surgeon places the tip of the probe 18 at each of the reference points 71, 73, and 75 on the patient, in turn, as directed by the computer program. This establishes a relationship between the locations of these reference points in the model space and their current physical locations in the predetermined coordinate system 80. In turn, this establishes a linear mathematical relationship between all points the model and coordinate system 80. Thereafter, if the patient is ever moved relative to the sensors, a new relationship must be defined by again digitizing the reference points 71, 73, and 75 within the coordinate system 80. That is, the correlation phase must be repeated. Thereafter, a surgeon can relate any locations of interest on the diagnostic images with the corresponding physical locations on his patient during an operation, and vice versa. These could be locations accessible to the probe tip 18 but not necessarily directly visible to the surgeon.

Having described the function and purpose of the preliminary steps, the detailed method of the present invention is more easily understood. As shown in FIG. 7, the position data 21 of the probe emitters 14, 16 generated by the sensors 20, 22, 24 and control unit 30 are converted into three-dimensional coordinates relative to the predetermined coordinate space of the sensors 20, 22, 24. Using dimensional parameters describing the relationship among the probe emitters 14, 16 and probe tip 18, the computer 36 determines the coordinates of the probe tip 22 in a step 39. During the correlation phase, the probe tip 22 is placed at each of the reference points 71, 73, and 75. Their coordinates in the sensor space along with their coordinates 46 in the image space determine a unique linear transformation relating the two spaces in a step 45. This is a known calculation in analytic geometry and matrix mathematics.

A more automated method of determining the locations of the reference points 71, 73, and 75 is to place other emitters 70, 72 and 74 (FIG. 1B) at those reference points and use the sensors 20, 22, 24 to determine their locations relative to the predetermined coordinate system 80 of the sensors. In that case, the correlation phase could be automatically initiated by the computer 36 except for the manual attachment of the additional emitters 70, 72, 74 at the reference points 71, 73, 75 just before using the device. In fact, the correlation phase could be frequently but briefly repeated from time to time (continuously or initiated by the operator), interspersed in the operational phase for the purpose of recalculating the linear transformations M and M' should the object (such as a surgical patient) move relative to the sensors 20, 22, 24.

During normal operation, the tip coordinates are transformed in a step 44 using the transformation computed in the step 45. The new transformed coordinates, relative to the image space, are used to determine the plane of some two-dimensional cross-section through the three-dimensional image model 41 accessible in the accessible memory 43. The simplest method is simply to choose the existing diagnostic image plane located closest to the probe tip's coordinates relative to the model space.

A more advanced method requires synthesizing a cross-sectional image at some other angle through the model using the data from multiple image slices.

In any case, a step 47 transforms the two-dimensional cross-sectional slice to a screen image and places a cursor on it to mark the location of the probe tip in the image space. Scaling and viewing parameters determine how the image is displayed. Because the surgeon cannot simultaneously view the patient (object) and the computer display screen, the step 47 would only be executed when a button on the probe is pressed, freezing the image and the position of the probe tip marker at that instant.

In a more complex variation of this invention, the computer system could generate the displayed image slice at an arbitrary angle, for example, in the plane perpendicular to the direction the probe is pointing. In simpler cases, the computer would simply display any one or more convenient image slices through the location of the probe tip. For example, the displayed slice might simply be the original CT slice closest to that location. In any case, the computer would then display on the image a cursor at the current position of the probe tip.

An alternative means to record the location of the reference points in the coordinate space of the imaging apparatus during the imaging phase employs an additional, separate instance of the three-dimensional position mensuration probe, sensors, control unit, and computer of the present invention. The additional sensors would be permanently attached directly on the imaging apparatus. The additional probe would measure the location of the reference points at the time of imaging, and the additional control unit and computer would determine and record their locations relative to the coordinate system of the imaging apparatus. The advantage of this approach is that the landmarks or reference pins need not be within the limited cross-sectional slices visible to the imaging device.

As an alternative to true three-dimensional images, standard x-ray radiographs from several distinct directions can be used to construct a crude model in lieu of the imaging phase described above. Radiographs from two or more directions would be digitally scanned, and four non-coplanar reference points on them would be identified with a cursor or light pen. In a correlation phase similar to that described above, these four points on the patient would be digitized just prior to surgery. Then, during surgery, the location of the probe tip would be projected onto digitized computer images of the two-dimensional radiographs where the projection is uniquely defined by mapping the reference point coordinates from the model space to the sensor spaces.

Lastly, a videotape recording of the computer screen (as well as the direct view of the surgeon and patient) could help document the performance of the procedure. Light emitters could be present on more than one standard surgical tool such as the microscope, scalpel, forceps, and cauterizer, each of which would in effect be a probe.

The method and apparatus of the optical mensuration and correlation apparatus 10 of the present invention has been completely described. While some of the obvious and numerous modifications and equivalents have been described herein, still other modifications and changes will readily occur to those skilled in the art. For instance, the preferred embodiment uses visible light, since human operators can readily observe if the light sources are operative or whether they are causing troublesome reflections. Clearly, other wavelengths of electromagnetic radiation could be used without departing from the spirit and scope of the invention. Infrared light would have the advantage of not distracting the surgeon with flashing lights. Other modifications to the detector optics and lenses are possible which would alter the image characteristics on the sensors. For example, toroidal lenses could be used which are longitudinally curved along an arc with a radius equal to the focal length of the lens. Similarly, the surfaces of the photodetectors could also be curved, thus allowing the images of distant light sources to remain in sharp focus, regardless of their positions. Various measurements of the detector outputs are also possible. For example, the angle of peak intensity, the intensity-weighted average, or the average of the minimum and maximum angles where the intensity is over some predetermined threshold value could be used. Finally, numerous enhancements of the digital data are possible by programming the computer to make the appropriate enhancements as would be obvious to those persons having ordinary skill in the art.

The foregoing is illustrative of the principles of the invention. Since numerous modifications and changes will readily occur to those skilled in the art given the teachings of the invention, it is not desired to limit the invention to the exact construction and operation shown and described. Accordingly, all suitable modifications and equivalents that may be resorted to in light of disclosure of the invention fall within the scope of the invention as defined by the following claims.

I claim:

1. Apparatus for determining the position and orientation of an invasive portion of a probe inside a three-dimensional body, wherein the probe includes an external portion that remains outside the body, comprising:

means defining a coordinate system wherein the three dimensional body is adapted to be disposed within said coordination system;

means defining an electronically displayable model of said body;

a probe comprising a portion adapted to be external to said three dimensional body and an invasive portion adapted to be internal to said three dimensional body;

at least two probe light emitters mounted in spaced relationship on the external portion of the probe each for projecting a probe light ray;

at least three light sensors, in known locations within said defined coordinate system, remotely located from the probe for detecting at least two probe light rays;

means to cause probe light rays to pass between said probe light emitters and said at least three light sensors which are non-linear with respect to each other;

means to measure angles between said probe light beams to at least three of said light sensors; and means coupled to said at least three light sensors for converting said angles to current locations of said probe light emitters and, from said locations, determining the position and orientation of the probe relative to said defined coordinate system and for deducing the position and orientation of the invasive portion of the probe by correlating the position and orientation of the probe relative to the defined coordinate system.

2. The apparatus of claim 1 further comprising display means coupled to said location determining means for indicating the position and orientation of the invasive portion of the probe by displaying a representation of the invasive portion of the probe tip in spacial relationship to a display of said model of the body.

3. The apparatus of claim 2 wherein said at least three light sensors comprises at least three one-dimensional light sensors in spaced relationship for sensing light rays from said probe light emitters.

4. The apparatus of claim 3 wherein each said one-dimensional light sensors comprises:

a linear photodetector; and a lens positioned between said linear photodetector and said probe light emitters for focusing light rays from said probe light emitters onto said linear photodetector.

5. The apparatus of claim 4 wherein each of said probe light emitters is strobed off and on by said computing means in a predetermined manner so that only one of said probe light emitters is illuminated at any one time.

6. The apparatus of claim 5 wherein each said lens of each said one-dimensional light sensor comprises a cylindrical lens.

7. The apparatus of claim 6 wherein said display means is a video monitor.

* * * * *